(12) United States Patent
Ries et al.

(10) Patent No.: US 11,751,949 B2
(45) Date of Patent: Sep. 12, 2023

(54) MEDICAL FASTENING DEVICE AND MEDICAL DEVICE

(71) Applicant: Joimax GmbH, Karlsruhe (DE)

(72) Inventors: Wolfgang Ries, Linkenheim (DE);
Rainer Steegmüller, Gerlingen (DE);
Sascha Telsemeyer, Karlsruhe (DE);
Johannes Thölking, Mannheim (DE)

(73) Assignee: Joimax GmbH, Karlsruhe (DE)

( * ) Notice: Subject to any disclaimer, the term of this patent is extended or adjusted under 35 U.S.C. 154(b) by 925 days.

(21) Appl. No.: 16/498,293

(22) PCT Filed: Mar. 14, 2018

(86) PCT No.: PCT/EP2018/000098
§ 371 (c)(1),
(2) Date: Sep. 26, 2019

(87) PCT Pub. No.: WO2018/177585
PCT Pub. Date: Oct. 4, 2018

(65) Prior Publication Data
US 2021/0100623 A1      Apr. 8, 2021

(30) Foreign Application Priority Data

Mar. 31, 2017   (DE) ..................... 10 2017 003 184.3
Sep. 15, 2017   (DE) ..................... 10 2017 008 655.9

(51) Int. Cl.
*B25B 5/00*       (2006.01)
*A61B 34/20*      (2016.01)
(Continued)

(52) U.S. Cl.
CPC .............. *A61B 34/20* (2016.02); *A61B 90/57* (2016.02); *B25B 5/101* (2013.01); *G01D 11/30* (2013.01);
(Continued)

(58) Field of Classification Search
USPC ..... 248/229.1, 226.11, 230.1, 230.2, 231.21, 248/231.31, 316.2, 316.3; 269/76, 66,
(Continued)

(56) References Cited

U.S. PATENT DOCUMENTS 2,888,928 A     6/1959   Seiger
4,547,092 A *  10/1985  Vetter ....................... F16B 2/04
                                                        248/229.11
(Continued)

FOREIGN PATENT DOCUMENTS

CN      103874525 A    6/2016
CN      106197603 A   12/2016
(Continued)

*Primary Examiner* — Alfred J Wujciak
(74) *Attorney, Agent, or Firm* — McGlew and Tuttle, P.C.

(57) ABSTRACT a medical fastening device for an electromagnetic sensor with a clamping element and with a sensor mount and to a medical device with such a fastening device, with an electromagnetic sensor and with a medical instrument. The clamping element has a counterpiece and a pressing piece movable relative to the clamping element, wherein the counterpiece has a lateral opening, which frees a free mounting area, which is itself at least partially enclosed by the counterpiece in a frame-like manner. The counterpiece has a depression, which points towards the mounting area and is arranged opposite the pressing piece, wherein the counterpiece is provided with an opening arranged opposite the depression. The pressing piece is movable in the opening in the direction of the depression of the counterpiece.

60 Claims, 10 Drawing Sheets

(51) Int. Cl.
  *B25B 5/10* (2006.01)
  *G01D 11/30* (2006.01)
  *A61B 90/57* (2016.01)
  *A61B 17/00* (2006.01)
  *B25B 5/02* (2006.01)

(52) U.S. Cl.
  CPC .............. *A61B 2017/00477* (2013.01); *A61B 2034/2051* (2016.02); *A61B 2034/2072* (2016.02); *A61B 2562/16* (2013.01); *B25B 5/00* (2013.01); *B25B 5/02* (2013.01)

(58) Field of Classification Search
  USPC ................ 269/138, 196–199, 217, 229, 236
  See application file for complete search history.

(56) References Cited

U.S. PATENT DOCUMENTS

| | | | | |
|---|---|---|---|---|
| 4,567,660 | A * | 2/1986 | Sakata | G01B 5/00 33/1 M |
| 5,228,323 | A * | 7/1993 | Dubinsky | B21D 41/021 72/317 |
| 5,836,559 | A * | 11/1998 | Ronci | A61G 13/101 248/230.1 |
| 6,089,111 | A | 7/2000 | Machijima | |
| 6,431,534 | B1 | 8/2002 | Orosz et al. | |
| 7,546,993 | B1 | 6/2009 | Walker | |
| 2002/0131818 | A1 * | 9/2002 | Wang | F16B 2/18 403/290 |
| 2005/0082729 | A1 * | 4/2005 | Wong | B23Q 3/069 269/91 |
| 2006/0043662 | A1 | 3/2006 | Blake | |
| 2009/0306499 | A1 | 12/2009 | Van Vorhis et al. | |
| 2011/0023343 | A1 | 2/2011 | Turner et al. | |
| 2011/0101587 | A1 | 5/2011 | Quintania et al. | |
| 2012/0209291 | A1 | 8/2012 | Anderson et al. | |
| 2014/0169860 | A1 * | 6/2014 | Meunier | F16B 2/06 403/187 |
| 2014/0200093 | A1 | 7/2014 | Parke et al. | |
| 2016/0089154 | A1 | 3/2016 | Chien et al. | |

FOREIGN PATENT DOCUMENTS

| | | |
|---|---|---|
| DE | 9301708 U1 | 5/1993 |
| DE | 19961827 A1 | 6/2001 |
| DE | 102006009115 A1 | 8/2007 |
| DE | 102010064389 A1 | 7/2012 |
| DE | 102013211055 B3 | 9/2014 |
| DE | 202015101401 U1 | 5/2015 |
| JP | 2009233331 A1 | 10/2009 |
| WO | 2010054836 A2 | 5/2010 |
| WO | 2014/147456 A1 | 9/2014 |
| WO | 2016049428 A1 | 3/2016 |

\* cited by examiner

Fig. 15 and claims the benefit of priority under 35 U.S.C. § 119 of German Applications 10 2017 003 184.3, filed Mar. 31, 2017, and 10 2017 008 655.9, filed Sep. 15, 2017, the entire contents of which are incorporated herein by reference.

MEDICAL FASTENING DEVICE AND MEDICAL DEVICE

CROSS REFERENCE TO RELATED APPLICATIONS

This application is a United States National Phase Application of International Application PCT/EP2018/000098, filed Mar. 14, 2018, and claims the benefit of priority under 35 U.S.C. § 119 of German Applications 10 2017 003 184.3, filed Mar. 31, 2017, and 10 2017 008 655.9, filed Sep. 15, 2017, the entire contents of which are incorporated herein by reference.

TECHNICAL FIELD

The present invention pertains to a medical fastening device for an electromagnetic sensor with a clamping element and with a sensor mount as well as to a medical device with such a device, with an electromagnetic sensor and with a medical instrument.

TECHNICAL BACKGROUND

A sensor such as a metal wire coil, which detects an electromagnetic field, especially an inhomogeneous electromagnetic navigation system, by field intensity and orientation, is called an electromagnetic sensor.

Minimally invasive surgeries are already carried out now by means of navigation-assisted surgical methods. Different navigation systems are used for this purpose. Active and passive systems are used. A part inserted into the body of a patient, such as an instrument or surgical tool, is provided in active systems with a transmitter, via which the position of the instrument or surgical tool, especially of the distal part thereof, which is located at the surgical site, can be determined externally. A field is generated in passive systems, and this field is detected by means of a sensor, as a result of which the position and the orientation of the instrument or surgical tool, especially of the distal end thereof, can, in turn, be detected directly or indirectly. Direct detection of the distal end of a surgical instrument comprises the arrangement of the sensor at the distal end of the instrument itself; indirect detection comprises the fixed, rigid arrangement of the sensor in a defined position, especially axial position, at the surgical instrument. The position and possibly the orientation of the distal end can be inferred on the basis of the measured sensor signal. Especially the electromagnetic navigation, in which an electromagnetic field is generated externally around the operating area, for example, by a generator of an electromagnetic field in a pillow, on which the patient lies, has proven to be effective in passive navigation. Coil-like sensors installed in the surgical instrument make it possible to locate the instruments, after which a visualization in CT or MRI images may be carried out. This process comprises no radiation exposure and thus reduces, on the whole, the radiation exposure, also due to a reduced use of X-rays. Neither is the image quality compromised, nor can sensors be hidden, because there are no optical sensors in the first place. The freedom of motion of the surgeon is not limited, unlike in the case of optical systems. The work of the surgeon is made substantially easier.

The fixed integration of sensors in surgical instruments would make these more expensive and cause, moreover, problems concerning sterilization. Sensor holders that can be fastened with their integrated sensors replaceably to surgical instruments and can thus also be used for different instruments are therefore provided. However, the arrangement of the holder and hence of the sensors is not trivial. Attempts were already made to fix a fully closed clamp carrying the sensor on an instrument. The clamp must be pushed here onto the respective instrument over the tip of the instrument up to the fastening site and fixed there. This surgical procedure with contaminated instruments is disadvantageous. Tissue remnants and liquids at the tip of the instrument may be transferred to the next instrument at the time of each change of instruments when pulling the holder over the tip of an instrument.

SUMMARY

A basic object of the present invention is to provide devices for fastening electromagnetic sensors as well as a comprehensive sensor device comprising a surgical instrument, an electromagnetic sensor and a fastening device, in which sensor device said drawbacks are avoided and, in particular, simple mounting and separation of the connection between the fastening device and the surgical instrument are possible in order thus to improve and optimize the handling.

This object is accomplished according to the present invention. Provisions are made for the clamping element to have a counterpiece and a pressing piece movable relative to the counterpiece. The counterpiece has a lateral opening, which frees a free mounting area, wherein the counterpiece encloses the mounting area at least partially in a frame-like manner. The counterpiece has a depression pointing towards the mounting area, which depression is arranged opposite the pressing piece. The counterpiece is provided with an opening arranged opposite the depression. The pressing piece can be moved in the opening in the direction of the depression of the counterpiece.

The object according to the present invention is accomplished, furthermore, by a medical device with the fastening device. The device according to the present invention is characterized in that the instrument can be inserted into the mounting area of the counterpiece, wherein the fastening device is detachably connected by clamping to the instrument and wherein the sensor is arranged in the sensor mount.

The present invention is based on the basic idea that a permanently secure relative position of the sensor in relation to the instrument must be guaranteed for a reliable determination of the position of the instrument. The sensor can be mounted on the medical instrument in an especially simple manner and rapidly by means of the fastening device according to the present invention. Sources of error in the adjustment, especially in connection with a surgical procedure, are avoided. Moreover, the clamping connection of the fastening device to the instrument can be released in a simple manner at any time, so that the fastening device can be used reusably with a plurality of instruments. Compared to the direct fastening of a sensor at the instrument, the user has more freedom in using the sensor, because the device can be used with different instruments.

The opening of the counterpiece may be configured as a threaded hole, the pressing piece being able to be moved in the threaded hole in the direction of the counterpiece by means of a screwing motion.

Provisions are preferably made for the depression to have first, opposite, straight sections extending at an angle in relation to one another and a second, curved end section, which connects the first sections. As a result, an especially simple, centered and repeatable position of the instrument is ensured at the fastening device. Based on the secure positioning of the instrument at the fastening device, the determination of the position of the instrument is less prone to errors. As an alternative hereto, the depression may have an exclusively circle segment-shaped configuration, the shape of the depression having especially radii of curvature in the range of 5 mm to 7.3 mm.

The pressing piece may have a jacket surface with a circumferential knurling in order to make simple handling possible for the user.

The counterpiece may have components consisting of plastic or metal, and may especially be made of these materials, the advantages of plastic being simple and rapid manufacture. By contrast, metal offers advantages in terms of robustness and wear of material.

In a preferred embodiment of the present invention, the pressing piece may be configured as a one-piece screw, which represents an especially simple configuration. The counterpiece is preferably configured as a one-piece, partially circumferentially open strap with two cheeks, which form end faces facing each other and have a finite distance from each other. The instrument can be inserted in this manner laterally through the intermediate space between the two cheeks into the free mounting area and can thus be fastened in a simple manner. The distance of the cheeks may be smaller than the diameter of the mounting area of the counterpiece in order to securely position the instrument in the mounting area. A risk of contamination due to contact of the device with a contaminated distal end of an instrument is avoided as a result.

In an advantageous variant of the present invention, the pressing piece has a carriage and a screwed part, the carriage being connected to the screwed part in a positive-locking manner, especially by means of a plug-type connection. Due to the multipart configuration of the pressing piece by means of a carriage and a screwed part, the carriage can be optimized, for example, concerning the possibility of positioning the instrument, while the screwed part may be configured for simple handling for the user. The connection between the carriage and the screwed part may be configured especially as a detachable connection, as a result of which one component or both components can be reused. As an alternative, the carriage may be permanently connected to the screwed part.

The carriage may be mounted rotatably at the screwed part in order to absorb rotary motions of the carriage in relation to the screwed part without the screwed part being subjected to mechanical stress.

On a side facing the carriage, the screwed part may have a pin, which can be caused to mesh with a recess of the carriage. As a result, the screwed part can be fastened to the carriage in an especially simple manner and rapidly. The recess of the carriage may now be arranged centered in relation to its cross section in order to set an unambiguous fastening position. The recess of the carriage may be configured as an opening.

In an especially advantageous embodiment, the pin has an attachment, which faces the carriage and whose cross section is larger than the cross section of the pin, the carriage having, on its end face facing the screwed part, a hole, whose diameter is smaller than the diameter of the recess, so that an undercut is formed between the hole and the recess and the attachment extends behind the undercut. An especially simple and reliable plug-type connection, which is not accidentally detachable due to unintentional motions, is configured in this manner.

The pin of the screwed part may be arranged within the recess of the carriage at a radially spaced location from the inner wall of the recess such that a radial clearance, which is especially useful when the carriage shall absorb tilting motions without mechanical stress, is formed between the pin and the recess. The attachment may be arranged for this purpose at an axially spaced location from the undercut such that an axial clearance is formed between the attachment and the undercut.

On a carriage end face facing the depression of the counterpiece, the carriage preferably has a groove with a circle segment-shaped cross section, so that the instrument can be clamped between the groove and the depression of the counterpiece. The advantage arises, in particular, that the instrument lies flatly in contact at both the groove and the depression and is held as a result in an especially mechanically stable manner. The groove may preferably be configured as a longitudinal groove and extend especially over the entire length of the carriage.

To simplify the plug-type connection between the carriage and the screwed part, the carriage may have at least one respective slot each at at least one of its jacket surfaces.

The counterpiece may have a plug or a holding part connected to the plug in a positive-locking manner. In particular, the plug may be detachably connected to the holding part, so that one component or both components can be reused.

The plug is preferably connected to the holding part by means of a locking and/or snap connection. Especially the plug may have for this purpose, on its end face facing the holding part, at least two locking hooks extending in the axial direction with a leg and with a hook-like projection, respectively, which can be caused to mesh with a respective recess of the holding part. The plug preferably has two, three or four locking hooks, which are arranged in pairs at equally spaced locations from one another on the end face of the plug. The locking hooks are especially preferably detachable by means of manual actuation.

In another embodiment, the holding part may have at least one actuatable projection for severing the connection between the plug and the holding part. This is especially useful in case of the use of a plurality of locking hooks in order to make it possible to sever the connection between the plug and the holding part rapidly and in a simple manner.

In order to make an especially simple handling by the user possible, the plug has a cylindrical end piece with a circumferential knurling at its end facing away from the holding part or the legs. Especially in connection with the knurling of the screwed part, the fastening device can be grasped and screwed by a user in an especially simple manner.

The sensor mount is preferably arranged in the counterpiece, especially in the plug thereof. The device is preferably formed from disposable components. The sensor mount may also be provided in the holding part. As a result, the sensor can also be replaced with an instrument having been clamped, without the connection between the instrument and the fastening device having to be severed.

In an especially advantageous configuration, the mount has a cross-shaped or V-shaped configuration, and at least one sensor line connected to the sensor can exit from the jacket surface of the plug or from the end face of the plug. The sensor mount may be provided with a cover, which reliably protects the sensor from external effects. The sensor mount may have a closable configuration, the closure being able to be welded or bonded to the fastening device. In particular, it proved to be advantageous to configure the sensor mount as a cross-shaped or V-shaped milled area.

Provisions may be made in variants for the device to have an electromagnetic sensor, which is configured as at least two helically wound coils arranged at a finite angle to one another.

The sensor is especially preferably configured as helically wound coils arranged in an X-shaped or V-shaped pattern in order to make it possible to exactly determine the position and the orientation of the clamping element/fastening device, including the position and the orientation of the sensor, in, for example, an externally applied electromagnetic field.

For an especially reliable positioning of the instrument, the instrument may be provided with a circumferential groove and the width of the carriage may correspond to the axial length of the circumferential groove of the instrument. An axial slipping of the instrument along the longitudinal direction thereof is prevented from occurring in this manner.

In one embodiment, the instrument lies, in the area of the circumferential groove, flatly on the second end section of the depression of the holding part and/or on the two sections extending at an angle in relation to one another on the groove of the carriage, so that the instrument can be arranged mechanically reproducibly at the fastening device.

Further advantages and features of the present invention appear from the claims and from the following description, in which exemplary embodiments of the present invention are explained in detail with reference to the drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
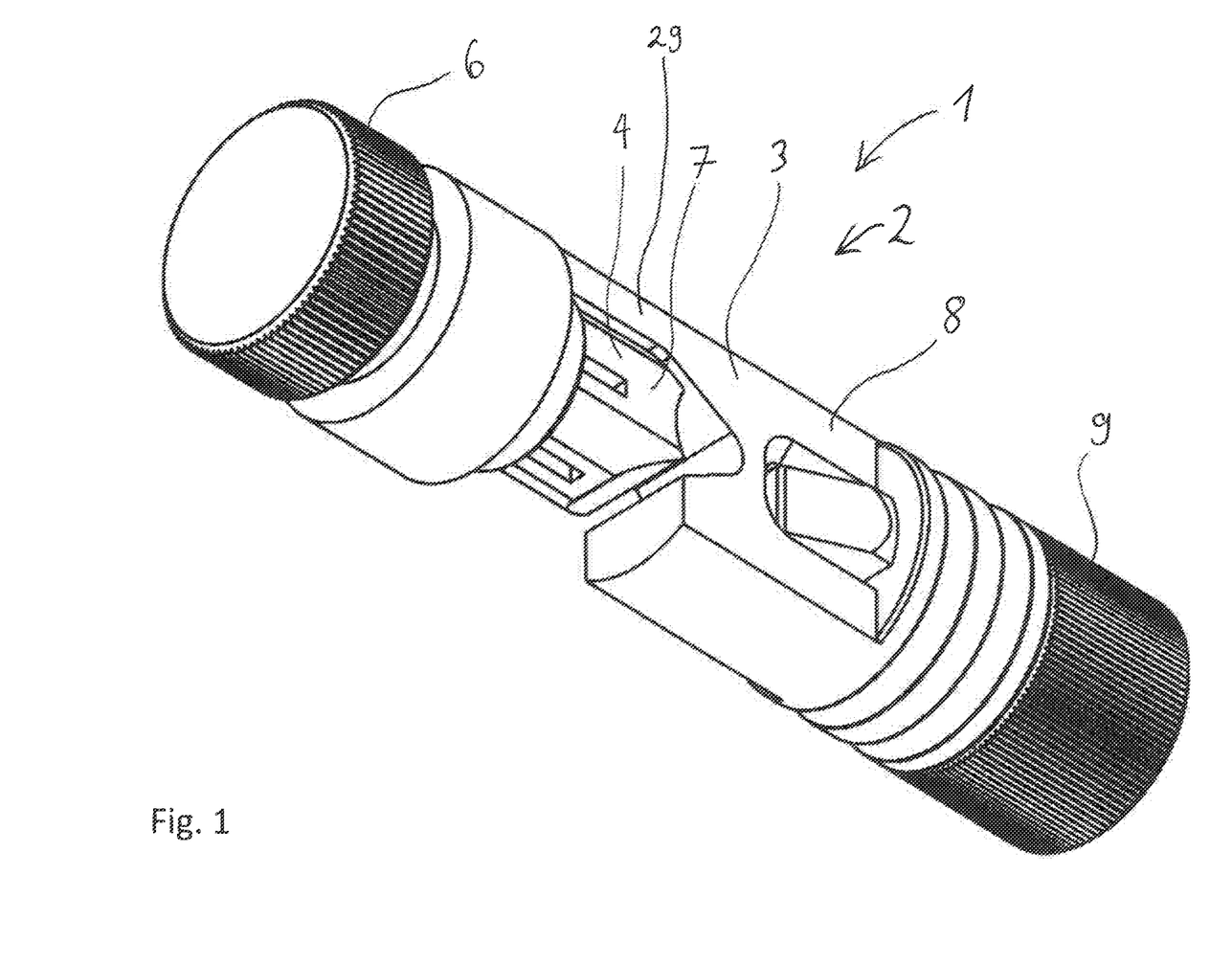
FIG. 1 is a perspective view showing a clamping element of a medical fastening device.

Referring to the drawings, FIG. 1 shows a medical fastening device 1 in a perspective view embodied as a clamping element 2, which has a pressing piece 4 arranged on the left side and a centerpiece 3 arranged on the right side. The pressing piece 4 is detachably connected to the counterpiece 3 via a holding area 29 and is axially movable relative to this along the holding area 29. A medical instrument 5 inserted between the counterpiece 3 and the pressing piece 4 can be clamped in the clamping element 2 in this manner, which will be described in detail below. In the embodiment shown in FIG. 1, the pressing piece 4 has a screwed part 6 and a carriage 7 and the counterpiece 3 has a holding part 8 and a plug 9, which will be described in detail below.

Figures 2, 3, 4:
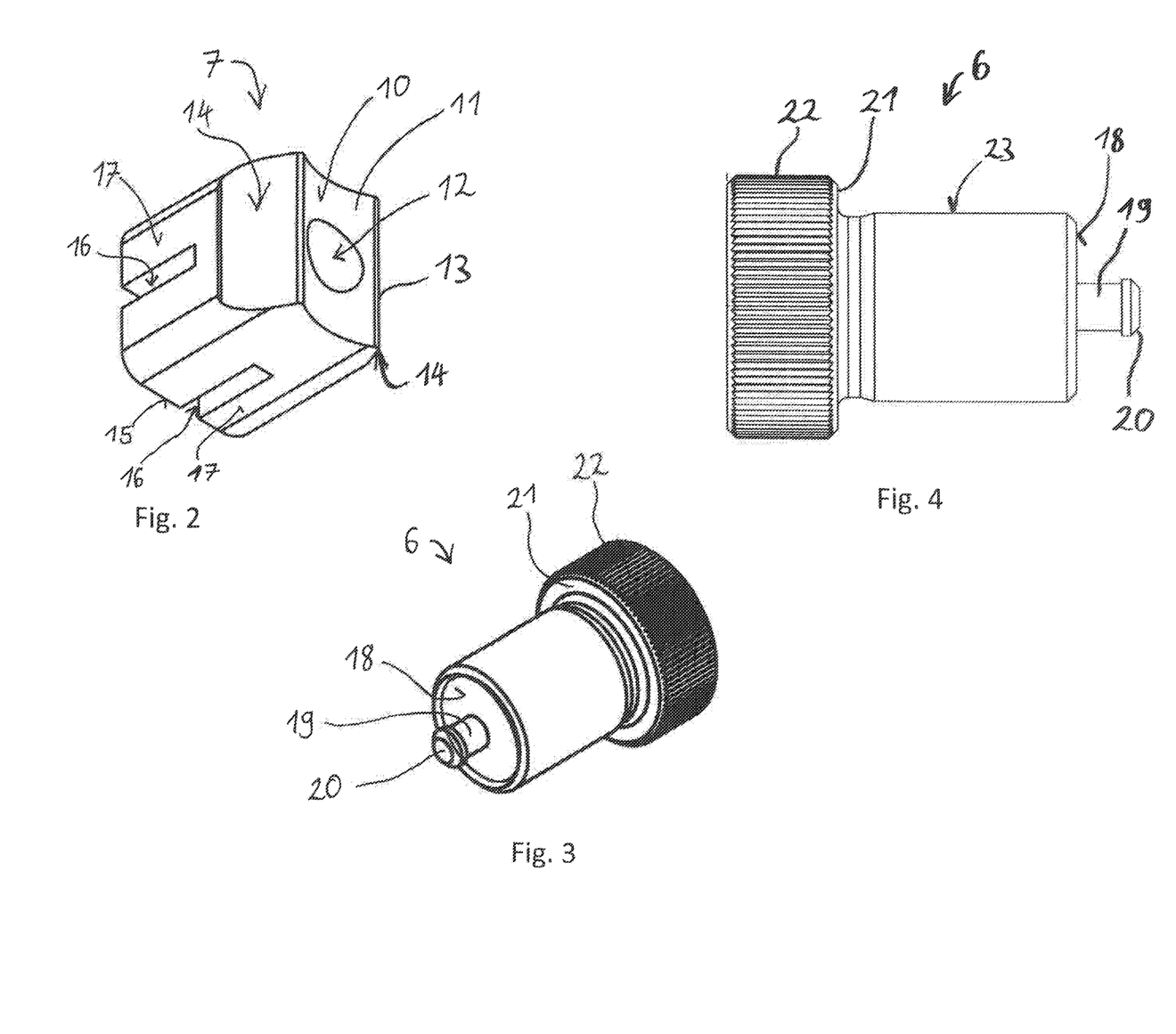
FIG. 2 is a perspective view showing a carriage of the pressing piece from FIG. 1.
FIG. 3 is a perspective view showing a screwed part of the pressing piece from FIG. 1.
FIG. 4 is a side view showing the screwed from FIG. 3.

The carriage 7 of the pressing piece 4 is shown in a perspective view in FIG. 2. On an end face 10 facing the counterpiece 3, a circular arc-shaped groove 11 is milled, which extends over the entire width of the carriage 7. A recess 12 with a circular cross section, which is configured as an opening or hole 12 in FIG. 2, is formed at mid-height of the groove 11. The groove 11 does not extend in the transverse direction over the entire cross section of the carriage 7, but over about one third of the cross section of the carriage 7. Beyond the two groove edges 13, a respective end area 14 of the carriage 7 is recessed with a beveled shape. On an end face 15 of the carriage 7 facing away from the groove 11, the carriage 7 has essentially a rectangular cross section with rounded corners. At mid-length of a respective side edge of the end face 15, a rectangular slot 16 is milled into an associated jacket surface 17 of the carriage 7, which slot 16 extends over approximately half of the height of the carriage 7.

Figure 10:
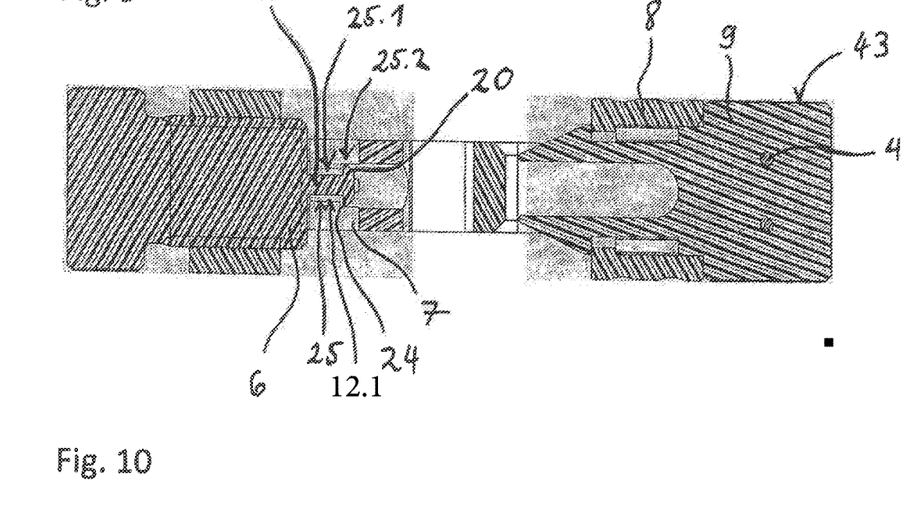
FIG. 10 is a schematic cross-sectional view showing the clamping element from FIG. 9.

Centrally from its end face 15, the carriage 7 has a hole 12.1, which extends over approximately half of the height of the slots 16, is flush with the hole 12 and passes over into same. However, the hole 12.1 has a smaller diameter than the hole 12, so that an undercut 24, which is seen in detail in FIG. 10, is formed at the transition of the two holes 12, 12.1.

FIG. 3 shows the screwed part 6 of the pressing piece 4, wherein the screwed part 6 has an essentially cylindrical shape. On an end face 18 facing the carriage 7, the screwed part 6 has a radially centered, cylindrical pin 19, which, facing the carriage 7, is provided with an attachment 20. The attachment 20 has a frustoconical configuration and has a larger diameter than the pin 19. The attachment 20 has a diameter larger than that of the hole 12.1 (while the diameter of the pin 19 is smaller than that of the hole 12.1 and smaller than that of the hole 12). On a side facing away from the pin 19, the screwed part 6 is provided with a base-shaped end piece 21, in the jacket surface of which a knurling 22 is milled. FIG. 4 shows the screwed part 6 from FIG. 3 in a side view. The jacket surface 23 of the screwed part 6 has an external thread, which is not shown in FIGS. 3 and 4.

Figure 5:
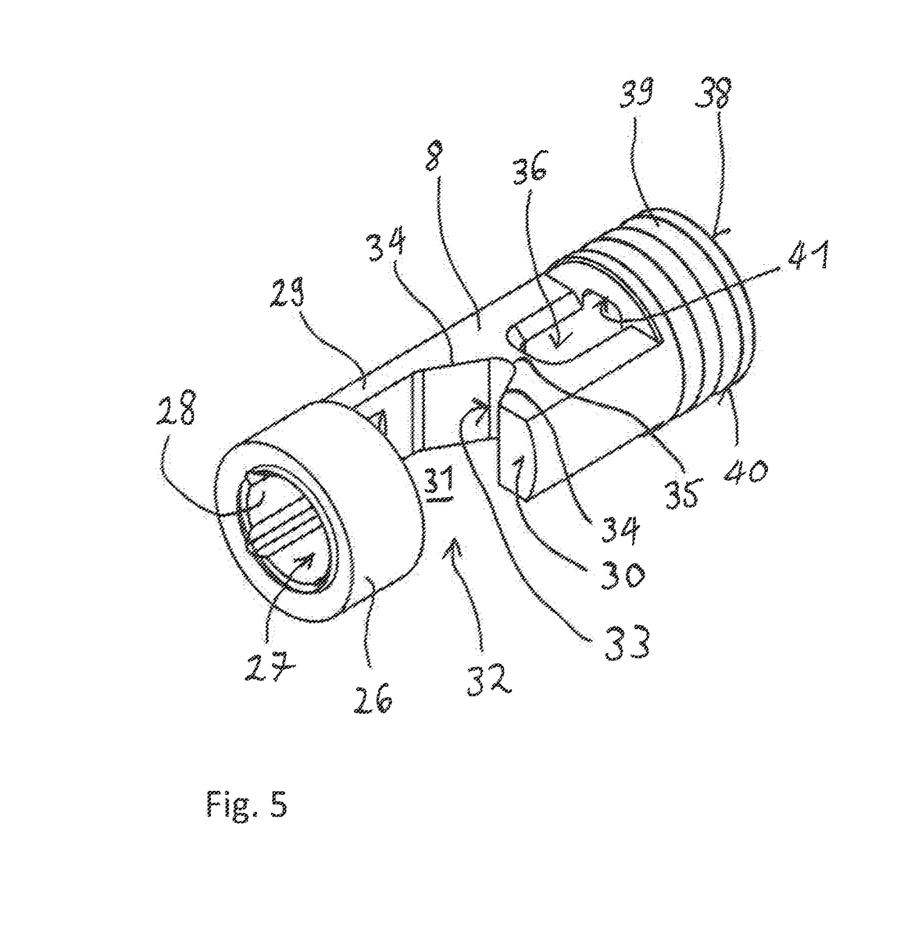
FIG. 5 is a perspective view showing a holding part of the counterpiece.

FIG. 5 shows the holding part 8 of the counterpiece 3, which has a hollow cylindrical attachment 26 with a centered opening 27 in an area facing the pressing piece 4. An inner wall 28 of the opening 27 is provided with an internal thread (not shown), so that the opening 27 is configured as a threaded hole. The thread of the inner wall 28 corresponds to the thread of the screwed part 6. On the side of the attachment 26 facing away from the screwed part 6, an arc-shaped holding area 29 is milled, which ends in an end face 30 pointing towards the attachment 26 and partially encloses an inner free mounting area 31 in a frame-like manner. A diameter 32 frees the mounting area 31 between the end face 30 and the attachment 26.

In a section located opposite the attachment 26, the holding area 29 has a depression, with first opposite, straight sections 34 extending at an angle in relation to one another and with a second, curved end section 35 arranged in a centered manner, which connects the two sections 34.

Figure 6:
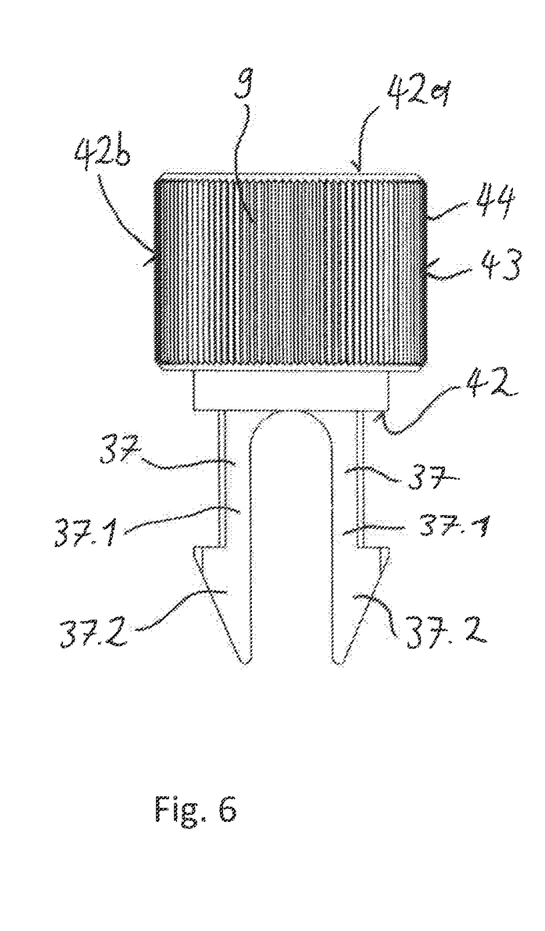
FIG. 6 is a side view showing a plug of the counterpiece.

Two rectangular recesses 36, which are located opposite each other and are configured as openings, are milled in an end area of the holding area 29, which end area faces away from the attachment 26, for receiving locking hooks 37 of the plug 9 (FIG. 6). On the end face 38 located opposite the attachment 26, a hollow cylindrical end piece 39 with a profiled jacket surface 40 is connected in one piece to the holding area 29. Recesses 41, with which the locking hooks 37 can be caused to mesh and which adjoin the openings 36, are milled in the radial inner surface of the end piece 39.

FIG. 6 shows the plug 9 in a side view. On an end face 42 facing the holding part 8, the two locking hooks 37, which extend in the longitudinal direction and are located opposite each other, are configured with a respective, axially extending leg 37.1 and with a hook-like projection 37.2, which can be caused to mesh with the openings 36 and the recesses 41 of the holding part 8. The plug 9 is connected to the holding part 8 in this manner. On an end face 42a facing away from the locking hook 37, the plug 9 has a cylindrical end piece 42b, whose jacket surface 43 is provided with a knurling 44. The knurling 44 is used, similarly to the knurling 22 of the screwed part 6, for the simple manual actuation of the device 1.

Figure 7:
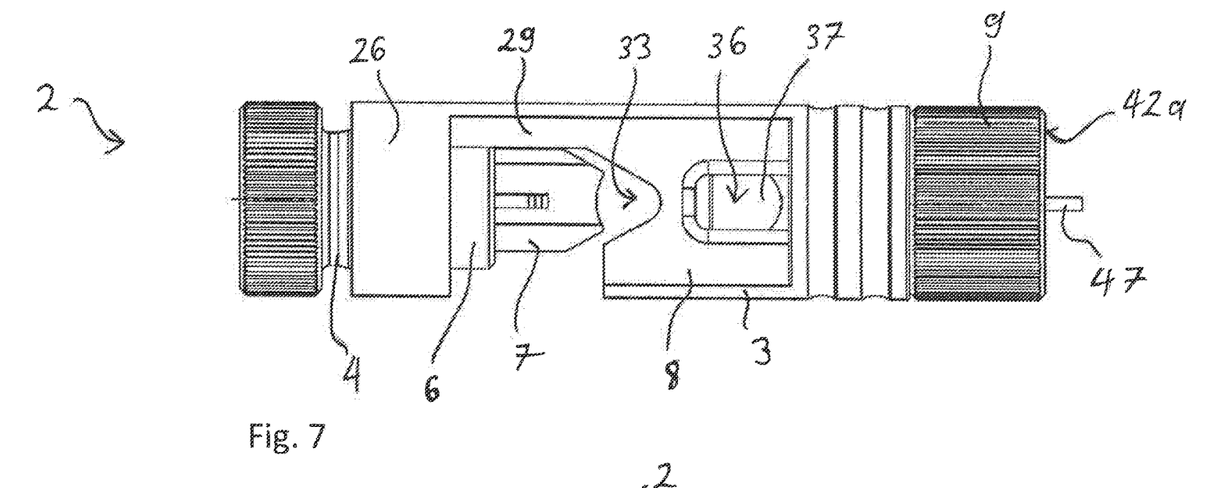
FIG. 7 is a side view showing the clamping element in a first configuration.
Figure 8:
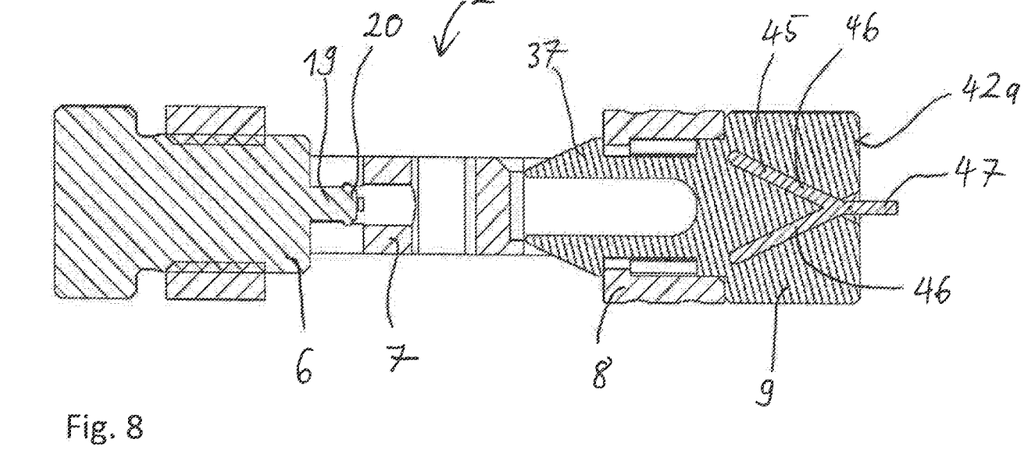
FIG. 8 is a schematic cross-sectional view showing the clamping element from FIG. 7.

FIG. 7 shows the fastening device 1 as an assembled clamping element 2, wherein the screwed part 6 of the pressing piece 4 is guided through the attachment 26 of the holding part 8 by means of a screwing motion. To fasten the screwed part 6 to the carriage 7, the screwed part 6 is pressed into the hole 12.1 of the carriage 7 with the pin 19 and with the attachment 20 from the end face 15 of the carriage 7. Based on the slots 16, the material areas remaining between these can yield, so that the attachment 20 can be pushed through the hole 12.1 despite the larger diameter compared to the diameter of the hole 12.1 until the attachment 20 enters the hole 12 and extends behind the undercut 24 at the transition of the holes 12, 12.1, as this is shown in FIGS. 8 and 10. The screwed part 6 and the carriage 7 are connected there inseparably, but rotatably in relation to one another, but the carriage 7 is prevented from performing a rotary motion over the entire circumference because of the holding area 29 of the holding part 8. The screwed part 6 and hence the pressing piece 4 are axially movable relative to the counterpiece 3 by means of the screwing motion. In particular, the carriage 7 is movable in this manner in the direction of the depression 33 of the holding part 8.

The connection of the plug 9 to the holding part 8 is seen in the carriage 7 shown on the right-hand side of FIG. 7. As was already mentioned above, the locking hooks 37 of the plug 9 pass through the recesses 41 and lock into openings 36 of the holding part 8, so that the plug 9 is connected to the holding part 8 in a positive-locking and detachable manner. To sever the connection, the locking hooks 37 are pushed by the user manually radially inwards and the plug 9 is then removed from the holding part 8.

An electromagnetic sensor 45 is provided in the plug 9 in the exemplary embodiment shown in FIG. 7, which appears especially from the longitudinal sectional drawing of FIG. 8 belonging to FIG. 7. It is seen there that the sensor 45 has two helically wound coils 46 made of, for example, metal wire insulated electrically by insulating varnish, wherein the metal wire, in particular, is jacketed by insulating varnish, and is bonded into the plug 9. A sensor line 47 connected to the sensor 45 exits from the plug 9 on the end face 42a facing away from the pressing piece 4. The coils 46 are in a V position in relation to one another and thus form a 6-DOF sensor.

Figure 9:
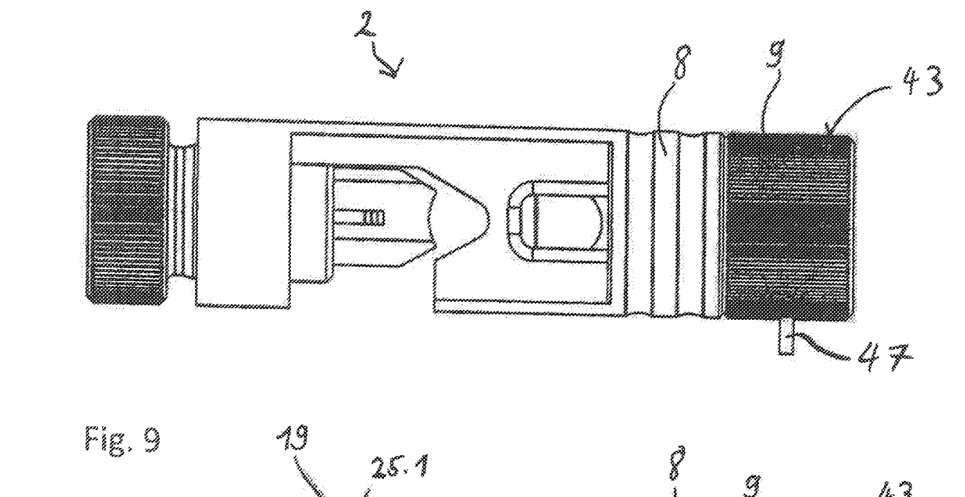
FIG. 9 is a side view showing the clamping element according to the present invention in a second configuration.

FIGS. 9 and 10 show a second embodiment of the clamping element 2, in which the sensor 45 is provided in the plug 9 in an arrangement shown at right angles to the longitudinal section plane of FIG. 10. The sensor line 47 exits from the jacket surface 43 of the plug 9 in this embodiment. A radial intermediate space or radial clearance 25.1 is formed between the pin 19 of the screwed part 6 and an inner wall 25 of the recess 12. In addition to the radial clearance 25.1 between the pin 19 and the inner wall 25, an axial clearance 25.2 is provided between the attachment 20 and the undercut 24, so that relative tilting between the screwed part 6 and the carriage can be absorbed more easily, with both axes having been brought out of alignment.

Figure 11:
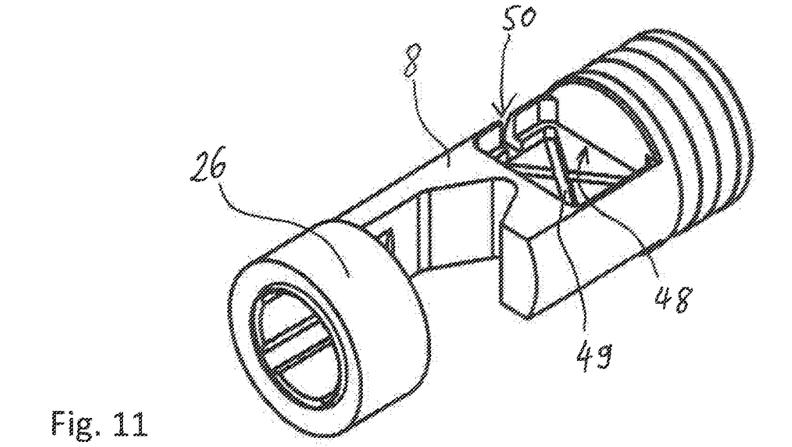
FIG. 11 is a perspective view showing the holding part in another configuration.
Figure 12:
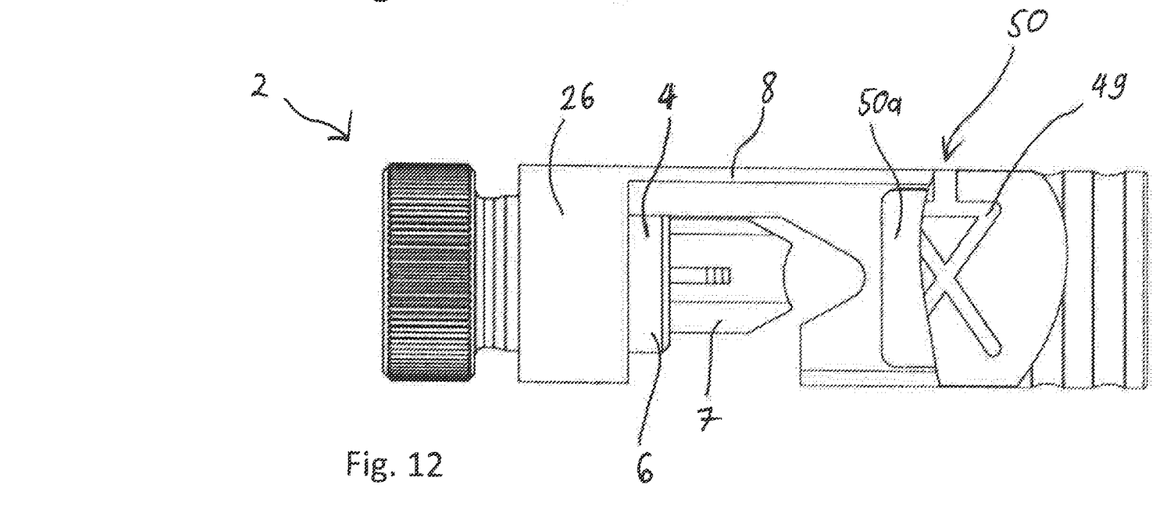
FIG. 12 is a schematic side view showing the holding part from FIG. 11 with a pressing piece.

FIG. 11 shows another embodiment of the holding part 8, which has a rectangular depression 48 with rounded corners in an area facing away from the attachment 26, and a cross-shaped groove 49 is milled into the bottom of said depression for inserting a corresponding sensor 45, so that the groove 49 is used as a sensor mount. The sensor lines 47 can be led out of the holding part 8 through a lateral opening 50 in this embodiment. FIG. 12 shows the configuration of the holding part 8 from FIG. 11 as a part of another embodiment of the device 2 in a schematic view, in which the area of the depression 48 is shown partially as a schematic longitudinal section in order to illustrate the positions of the milled area 49 and of the opening 50. The depression 48 may be detachably closed, especially bonded, with a cover 50a, in order to protect the sensor 45 or the sensor mount 49 from contamination. As an alternative, the cover 50a may be welded to the depression 48. According to FIG. 12, the pressing piece 4 comprising the screwed part 6 and the carriage 7 is connected to the holding part 8.

Figures 13, 14:
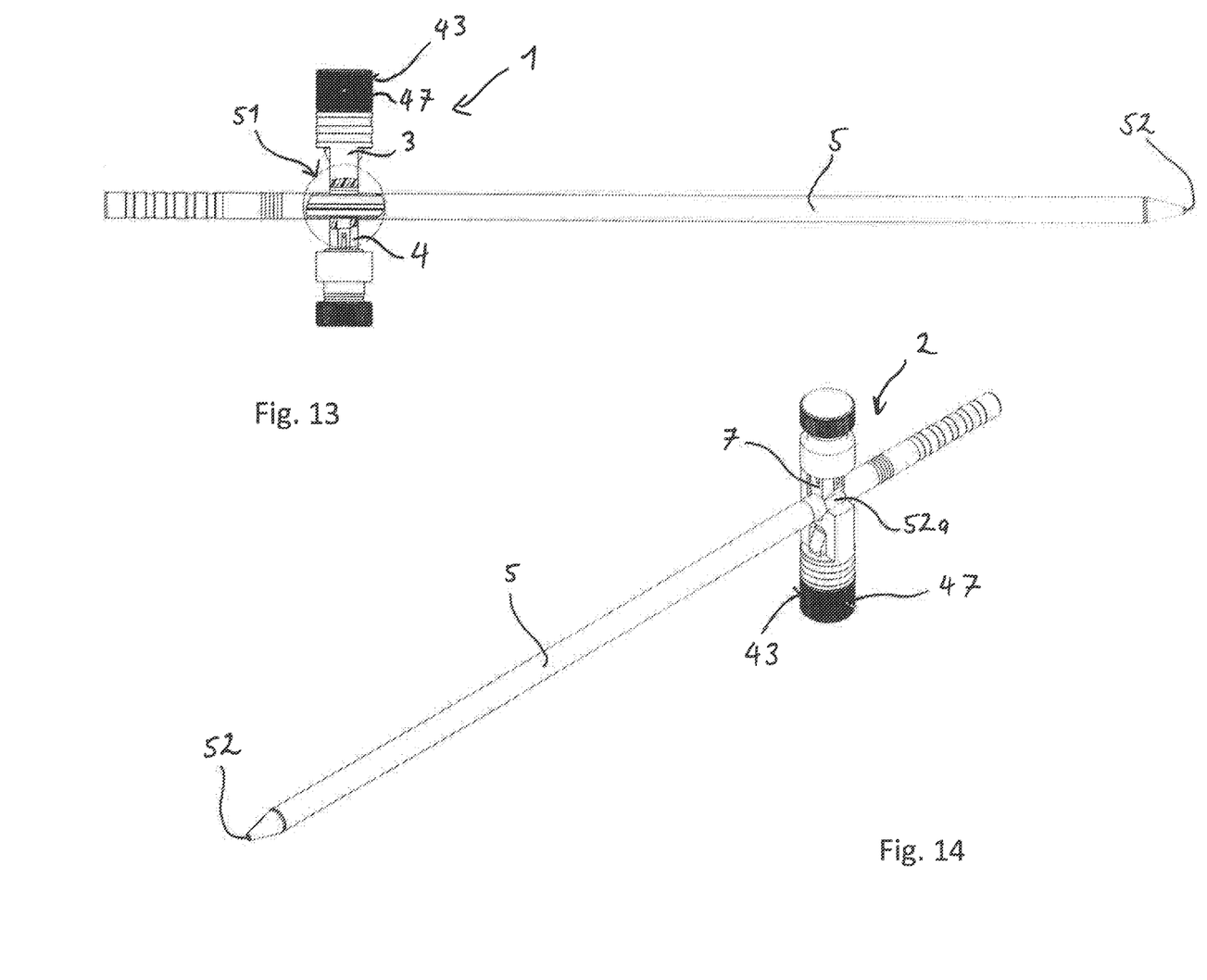
FIG. 13 is a side view showing a medical device according to the present invention with a fastening device and with a medical instrument in a side view.
FIG. 14 is a perspective view, obliquely from the top, showing the medical device from FIG. 13.

FIG. 13 shows the medical fastening device 1 according to the present invention, in which an oblong medical instrument 5 is clamped between the pressing piece 4 and the counterpiece 3. The connection area 51 is shown in the longitudinal section for the sake of greater clarity. Due to the arrangement shown in FIG. 13, the sensor 45 arranged in the plug 9 assumes a permanently fixed relative position in relation to a distal tip 52 of the instrument 5. If the position of the sensor 9 is determined on the basis of common methods, for example, within an externally applied electromagnetic field, the position in space and the orientation of the distal tip 52 of the instrument 5 can be inferred from these pieces of information.

FIG. 14 shows the arrangement from FIG. 13 in a perspective view, from which it appears that the instrument 5 is provided in the connection area 51 with a depression 52a configured as a ring groove, whose length corresponds to the length of the groove 11 of the carriage 7. The axial longitudinal position of the device 1 at the instrument 5 can be determined in this manner. The exit of the sensor line 47 from the jacket surface 43 of the plug 9 is shown in FIGS. 13 and 14.

FIGS. 15 through 18 show another embodiment of the fastening device according to the present invention, and FIGS. 19 through 22 show a medical device according to the present invention with such a device.

Figures 15, 16, 17:
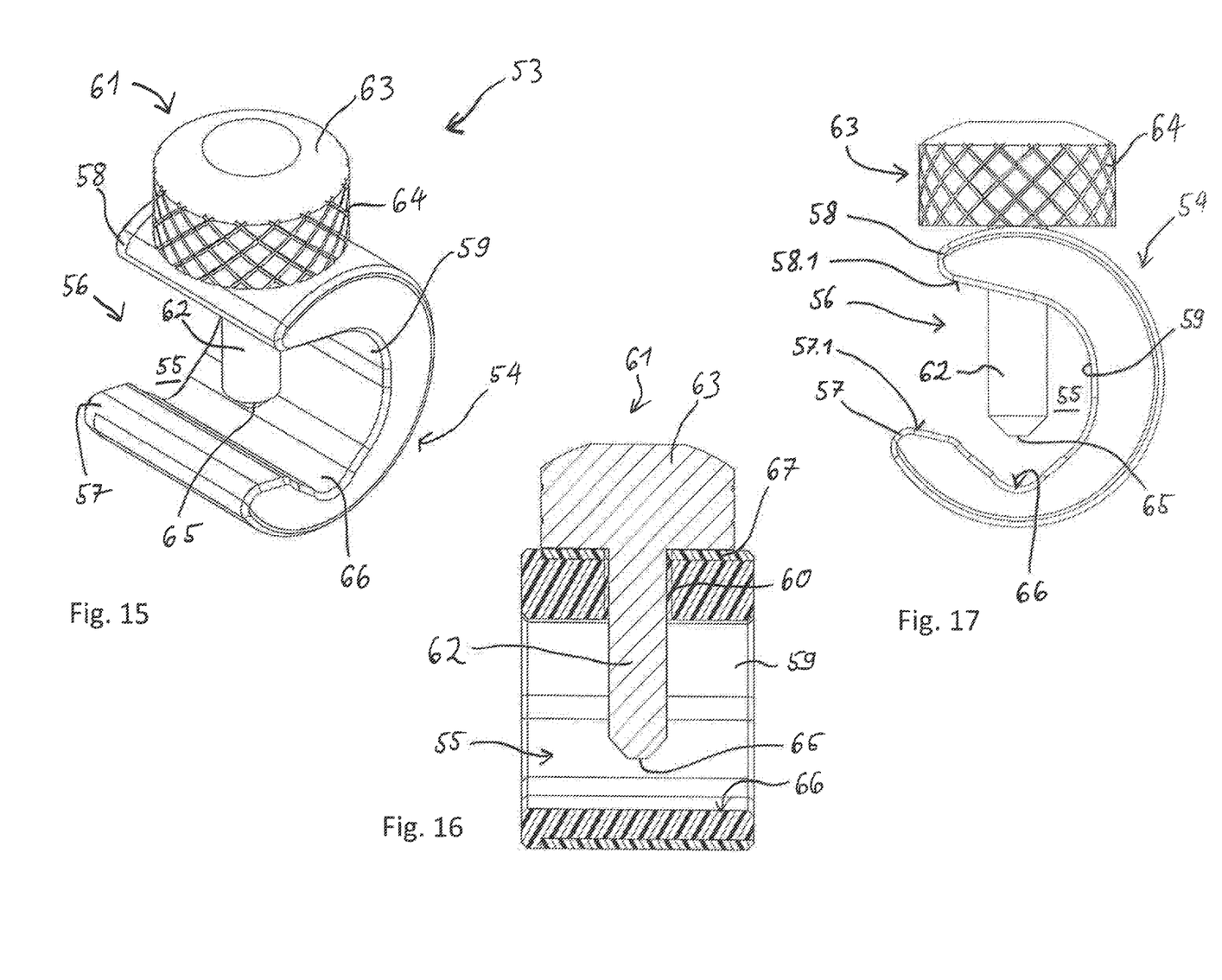
FIG. 15 is a perspective view showing another configuration of the device according to the present invention.
FIG. 16 is a sectional view showing a section through the view shown in FIG. 15.
FIG. 17 is a side view showing a top view of the device according to FIG. 15.
Figures 18, 19:
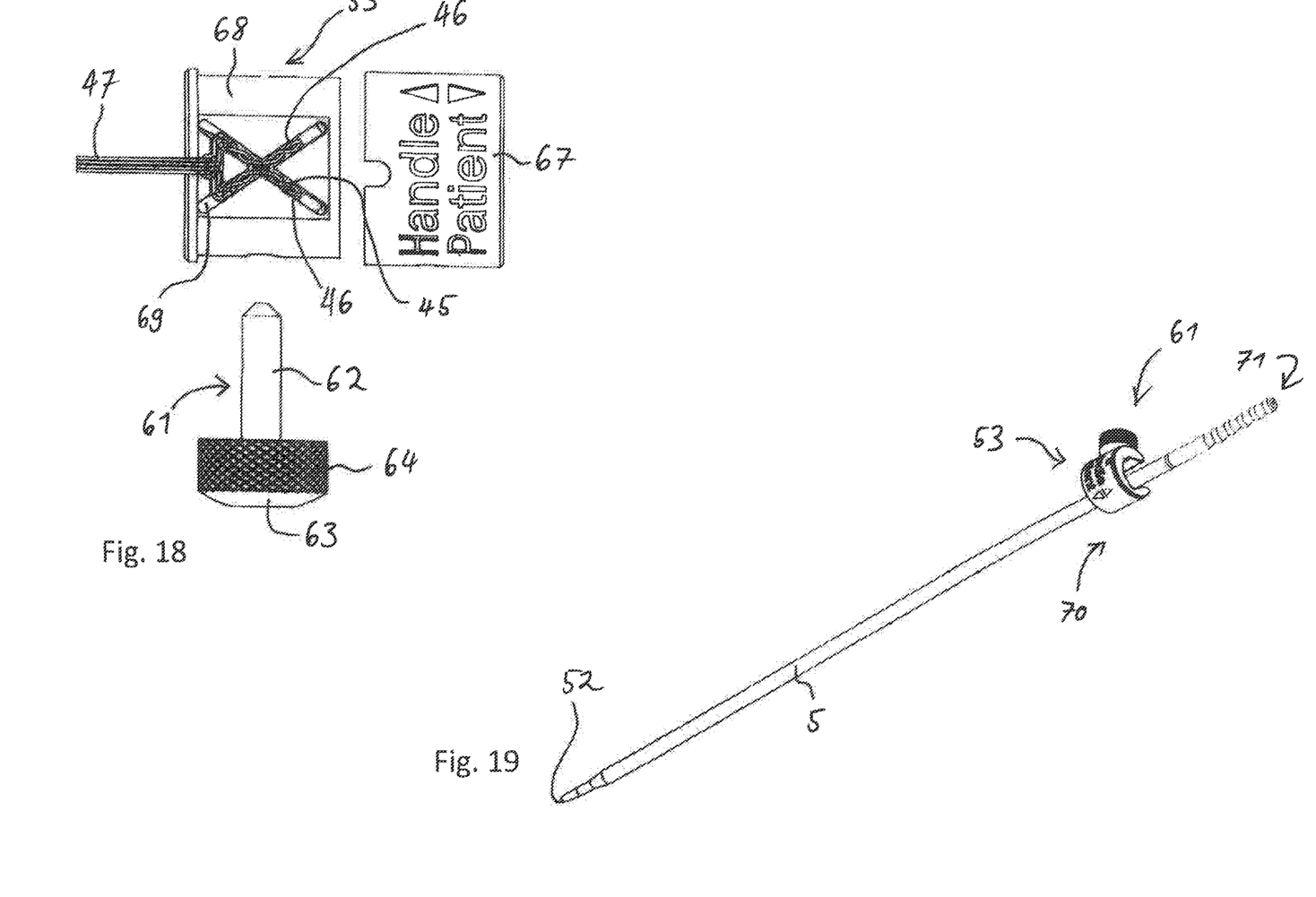
FIG. 18 is an exploded view through the device according to FIG. 15 with the circumferential jacket or cover removed and with the sensor being visible as a result.
FIG. 19 is a perspective view showing a second sensor device with the device according to FIGS. 15 through 18.
Figure 20:
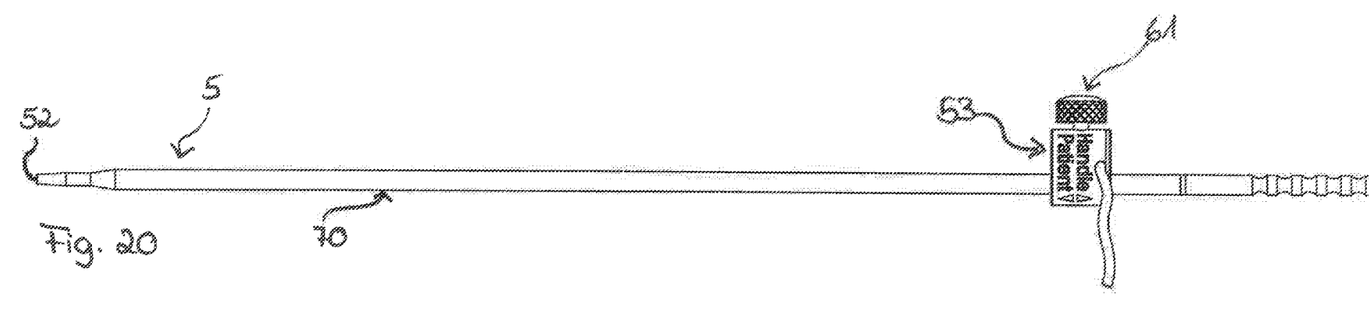
FIG. 20 is a side view of the device from FIG. 19.
Figure 21:
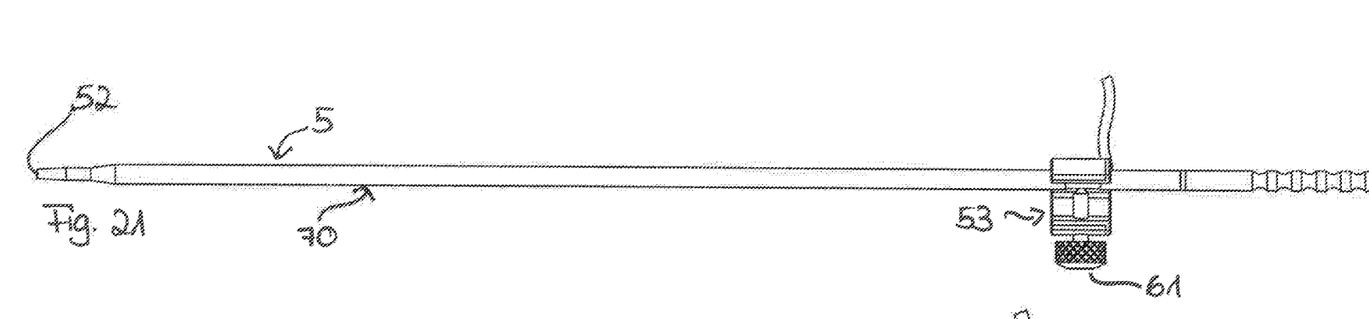
FIG. 21 is a side view, which is rotated by 180° about the longitudinal axis in relation to FIG. 20.

The device 53 according to the present invention according to FIGS. 15 through 18 encloses an interior space 55 with a partly circular strap 54 and it likewise has a lateral opening 56, just like the above-described devices 1. The distance of the free end faces of the strap 54 and the size of the opening 56 are smaller than the diameter of the enclosed interior space 55 (FIG. 17). The end areas of partial arcs, which face away from the free end faces 57.1, 58.1 of the individual cheeks 57, 58, which said end faces face the opening 56, are connected in this embodiment in one piece to one another or pass over into one another in one piece, so that the cheeks form a rigid, one-piece partly ring-shaped strap 54 with inner longitudinal walls 59. This strap 54 has, close to the end face 58.1, a radial threaded hole 60, into which a screw 61 with a screw barrel 62 provided with external threads and with a screw head 63 with a circumferential knurling 64 is screwed. Located opposite the inner free end 65 of the screw barrel 61, the inner side of the strap 54 is provided with an inner mount 66, which may have, for example, a prismatic configuration and has a configuration similar to the depression 33 of the above-described embodiments.

Under a cover 67, which can be pushed over axially, the device 53 has, in an inner part 68 of the strap 54, a mount 69 in the form of a cross-shaped depression, into which the sensor 45, which can be connected to an analysis unit via the sensor lines 47, is bonded.

The device 53 can be attached to a surgical instrument, tool or surgical part 5 laterally or radially (FIGS. 19 through 22) by the screw 61 being screwed back, so that the interior space 55 of the strap 54 is freed, and the surgical instrument 5 can enter into the interior space 55 when the device 53 is attached to said surgical instrument. The screw is then screwed inwards, as a result of which the surgical instrument 5 is pressed into the mount 66 and the device 53 is fixed at the surgical instrument 5 on further screwing. A long screw thread of the screw and the configuration of the longitudinal walls 59 of the device 53 make use possible for a wide range of diameters.

Figure 22:
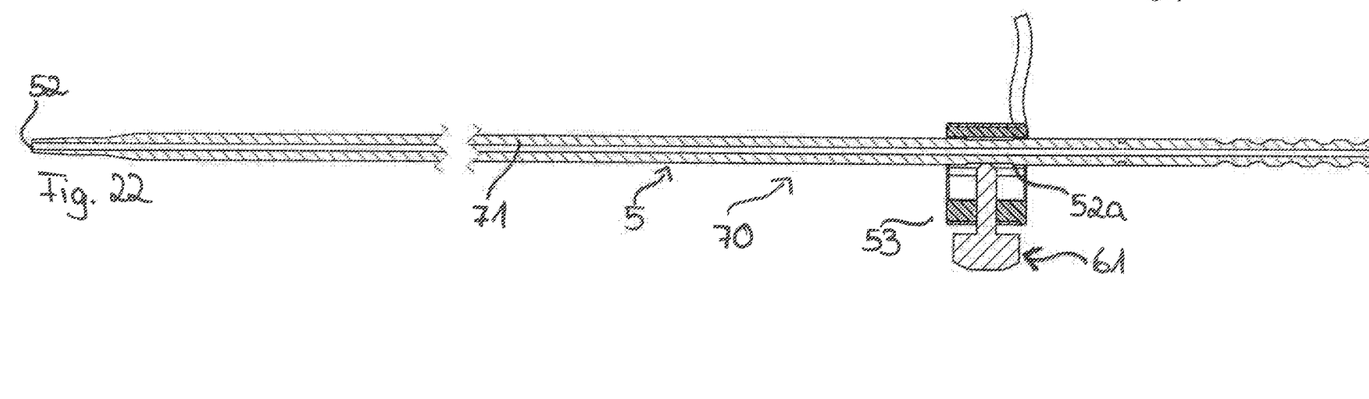
FIG. 22 is a longitudinal sectional view through the device according to FIGS. 19 through 21.

According to FIGS. 19 through 22, a preferred embodiment of the overall sensor device 70 is formed by a surgical instrument, tool or surgical part 5 and by a device 53, which was described above, fixed to this. The surgical instrument 5 has a circumferential groove 52a here as well, as a result of which the device 53 is fixed or positioned in an axially defined manner at the instrument 5, so that the exact position of the distal tip 52 of the surgical instrument 5 can again be determined in case of measurement of the device 53 or via the sensor 45 located in said device. As is shown in FIG. 22, the surgical instrument 5 may be a cannulated instrument, i.e., it may have an axial opening 71, as it can be seen in the sectional view shown in FIG. 22, so that the device 70 can be inserted into a patient via a wire, such as via a Seldinger wire.

While specific embodiments of the invention have been shown and described in detail to illustrate the application of the principles of the invention, it will be understood that the invention may be embodied otherwise without departing from such principles.

The invention claimed is:

1. A medical fastening device for an electromagnetic sensor, the fastening device comprising:
   a clamping element; and
   a sensor mount, wherein the clamping element comprises a counterpiece and a pressing piece movable relative to the counterpiece, wherein the counterpiece has a lateral opening, which frees defines a laterally open a free mounting area and another opening, wherein the counterpiece comprises a partial frame, that partially encloses the mounting area at least as a partial frame, wherein the counterpiece has a depression, which points towards the mounting area and which is arranged opposite the pressing piece, wherein the other opening of the counterpiece is provided with an opening arranged opposite the depression, and wherein the pressing piece is movable in the other opening in the direction towards and away from the depression of the counterpiece to releasable mount the sensor mount, and further in combination with the electromagnetic sensor mounted on the sensor mount, wherein the electromagnetic sensor is configured as at least two helically wound coils arranged at a finite angle in relation to one another.

2. A medical fastening device in accordance with claim 1, wherein the depression has first, opposite, straight sections extending at an angle in relation to one another and a second, curved end section, which connects the first sections.

3. A medical fastening device in accordance with claim 1, wherein the pressing piece is configured as a one-piece screw.

4. A medical fastening device in accordance with claim 1, wherein the pressing piece has a carriage and a screwed part, wherein the carriage is positive-locking connected to the screwed part.

5. A medical fastening device in accordance with claim 4, wherein the carriage is mounted rotatably at the screwed part.

6. A medical fastening device in accordance with claim 4, wherein the screwed part has, on an end face, facing the carriage, the screwed part has and a screwed part pin on the end face, which screwed part pin is meshable can be caused to mesh with a recess of the carriage.

7. A medical fastening device in accordance with claim 6, wherein:
   the pin has an attachment, which faces the carriage and the attachment has a cross section that is larger than a cross section of the pin;
   the carriage has, on a carriage end face facing the screwed part, a hole, the hole having a diameter that is smaller than a diameter of the recess, so that an undercut is formed between the hole and the recess; and
   the attachment extends behind the undercut.

8. A medical fastening device in accordance with claim 7, wherein the attachment is arranged at an axially spaced location from the undercut such that an axial clearance is formed between the attachment and the undercut.

9. A medical fastening device in accordance with claim 6, wherein the pin of the screwed part is arranged within the recess of the carriage at a radially spaced location from the inner wall of the recess such that a radial clearance is formed between the pin and the recess.

10. A medical fastening device in accordance with claim 4, wherein the carriage has a groove having a circle segment-shaped section on a groove end face facing the depression.

11. A medical fastening device in accordance with claim 4, wherein the counterpiece has a plug and a holding part positive-locking connected to the plug.

12. A medical fastening device in accordance with claim 11, wherein the plug is detachably connected to the holding part.

13. A medical fastening device in accordance with claim 11, wherein the plug is connected to the holding part by a locking connection and/or snap connection.

14. A medical fastening device in accordance with claim 13, wherein the plug has, on a plug end face facing the holding part, at least two locking hooks extending in an axial direction with a respective leg and with a respective projection, which can be caused to mesh with a recess of the holding part.

15. A medical fastening device in accordance with claim 11, wherein the plug has, at a plug end facing away from the holding part and the legs, a cylindrical end piece with a circumferential knurling.

16. A medical fastening device in accordance with claim 1, wherein the sensor mount is arranged in the counterpiece.

17. A medical fastening device in accordance with claim 1, wherein the sensor mount has a cross-shaped or V-shaped configuration.

18. A medical fastening device in accordance with claim 1, wherein the sensor mount is provided with a cover.

19. A medical fastening device in accordance with claim 1, in combination with the electromagnetic sensor and further in combination with a medical instrument, wherein the medical instrument is insertable into the mounting area of the counterpiece, wherein the fastening device is detachably connected by clamping to the medical instrument, and wherein the sensor is arranged in the mount.

20. A medical fastening device in accordance with claim 19, wherein the medical instrument is provided with a circumferential groove and a width of the carriage corresponds to an axial length of the circumferential groove of the medical instrument.

21. A medical fastening device in accordance with claim 20, wherein the medical instrument lies in an area of the circumferential groove flatly on the second end section of the depression of the holding part and/or on the groove of the carriage.

22. A medical fastening device for an electromagnetic sensor, the fastening device comprising:
 a clamping element; and
 a sensor mount, wherein the clamping element comprises a counterpiece and a pressing piece movable relative to the counterpiece, wherein the counterpiece has a lateral opening, which defines a laterally open mounting area and another opening, wherein the counterpiece comprises a partial frame, that partially encloses the mounting area, wherein the counterpiece has a depression, which points towards the mounting area and which is arranged opposite the pressing piece, wherein the other opening of the counterpiece is arranged opposite the depression, and wherein the pressing piece is movable in the other opening in the direction towards and away from the depression of the counterpiece to releasable mount the sensor mount, wherein the pressing piece comprises a carriage and a screwed part, wherein the carriage is positive-locking connected to the screwed part, wherein the counterpiece has a plug and a holding part positive-locking connected to the plug and wherein the plug has, at a plug end facing away from the holding part and legs, a cylindrical end piece with a circumferential knurling.

23. A medical fastening device in accordance with claim 22, wherein the depression has first, opposite, straight sections extending at an angle in relation to one another and a second, curved end section, which connects the first sections.

24. A medical fastening device in accordance with claim 22, wherein the carriage is mounted rotatably at the screwed part.

25. A medical fastening device in accordance with claim 22, wherein the screwed part has an end face facing the carriage and a screwed part pin on the end face, which pin is meshable with a recess of the carriage.

26. A medical fastening device in accordance with claim 25, wherein the pin of the screwed part is arranged within the recess of the carriage at a radially spaced location from the inner wall of the recess such that a radial clearance is formed between the pin and the recess.

27. A medical fastening device in accordance with claim 26, wherein the attachment is arranged at an axially spaced location from the undercut such that an axial clearance is formed between the attachment and the undercut.

28. A medical fastening device in accordance with claim 25, wherein:
 the pin has an attachment, which faces the carriage and the attachment has a cross section that is larger than a cross section of the pin;
 the carriage has, on a carriage end face facing the screwed part, a hole, the hole having a diameter that is smaller than a diameter of the recess, so that an undercut is formed between the hole and the recess; and
 the attachment extends behind the undercut.

29. A medical fastening device in accordance with claim 22, wherein the carriage has a groove having a circle segment-shaped section on a groove end face facing the depression.

30. A medical fastening device in accordance with claim 22, wherein the plug is detachably connected to the holding part.

31. A medical fastening device in accordance with claim 22, wherein the plug is connected to the holding part by a locking connection and/or snap connection.

32. A medical fastening device in accordance with claim 31, wherein the plug has, on a plug end face facing the holding part, at least two locking hooks extending in an axial direction with a respective leg and with a respective projection, which can be caused to mesh with a recess of the holding part.

33. A medical fastening device in accordance with claim 22, wherein the sensor mount is arranged in the counterpiece.

34. A medical fastening device in accordance with claim 22, wherein the sensor mount has a cross-shaped or V-shaped configuration.

35. A medical fastening device in accordance with claim 22, wherein the sensor mount is provided with a cover.

36. A medical fastening device in accordance with claim 22, further comprising the electromagnetic sensor, which is configured as at least two helically wound coils arranged at a finite angle in relation to one another.

37. A medical fastening device in accordance with claim 22, in combination with the electromagnetic sensor and in combination with a medical instrument, wherein the medical instrument is insertable into the mounting area of the counterpiece, wherein the fastening device is detachably connected by clamping to the medical instrument, and wherein the sensor is arranged in the mount.

38. A medical fastening device in accordance with claim 37, wherein the medical instrument is provided with a circumferential groove and a width of the carriage corresponds to an axial length of the circumferential groove of the medical instrument.

39. A medical fastening device in accordance with claim 38, wherein the medical instrument lies in an area of the circumferential groove flatly on the second end section of the depression of the holding part and/or on the groove of the carriage.

40. A medical fastening device for an electromagnetic sensor, the fastening device comprising:
 a clamping element; and
 a sensor mount, wherein the clamping element comprises a counterpiece and a pressing piece movable relative to the counterpiece, wherein the counterpiece has a lateral opening, which defines a laterally open mounting area and another opening, wherein the counterpiece comprises a partial frame, that partially encloses the mounting area, wherein the counterpiece has a depression, which points towards the mounting area and which is arranged opposite the pressing piece, wherein the other opening of the counterpiece is arranged opposite the depression, and wherein the pressing piece is movable in the other opening in the direction towards and away from the depression of the counterpiece to releasable mount the sensor mount, and in combination with the electromagnetic sensor mounted on the sensor mount and in combination with a medical instrument, wherein the medical instrument is insertable into the mounting area of the counterpiece, wherein the fastening device is detachably connected by clamping to the medical instrument, and wherein the sensor is arranged in the mount.

41. A medical fastening device in accordance with claim 40, wherein the depression has first, opposite, straight sections extending at an angle in relation to one another and a second, curved end section, which connects the first sections.

42. A medical fastening device in accordance with claim 41, wherein the screwed part has an end face facing the carriage and a screwed part pin on the end face, which pin is meshable with a recess of the carriage.

43. A medical fastening device in accordance with claim 42, wherein:
 the pin has an attachment, which faces the carriage and the attachment has a cross section that is larger than a cross section of the pin;
 the carriage has, on a carriage end face facing the screwed part, a hole, the hole having a diameter that is smaller than a diameter of the recess, so that an undercut is formed between the hole and the recess; and
 the attachment extends behind the undercut.

44. A medical fastening device in accordance with claim 43, wherein the attachment is arranged at an axially spaced location from the undercut such that an axial clearance is formed between the attachment and the undercut.

45. A medical fastening device in accordance with claim 42, wherein the pin of the screwed part is arranged within the recess of the carriage at a radially spaced location from the inner wall of the recess such that a radial clearance is formed between the pin and the recess.

46. A medical fastening device in accordance with claim 40, wherein the pressing piece is configured as a one-piece screw.

47. A medical fastening device in accordance with claim 40, wherein the pressing piece has a carriage and a screwed part, wherein the carriage is positive-locking connected to the screwed part.

48. A medical fastening device in accordance with claim 47, wherein the carriage is mounted rotatably at the screwed part.

49. A medical fastening device in accordance with claim 47, wherein the carriage has a groove having a circle segment-shaped section on a groove end face facing the depression.

50. A medical fastening device in accordance with claim 47, wherein the counterpiece has a plug and a holding part positive-locking connected to the plug.

51. A medical fastening device in accordance with claim 50, wherein the plug is detachably connected to the holding part.

52. A medical fastening device in accordance with claim 50, wherein the plug is connected to the holding part by a locking connection and/or snap connection.

53. A medical fastening device in accordance with claim 52, wherein the plug has, on a plug end face facing the holding part, at least two locking hooks extending in an axial direction with a respective leg and with a respective projection, which can be caused to mesh with a recess of the holding part.

54. A medical fastening device in accordance with claim 50, wherein the plug has, at a plug end facing away from the holding part, a cylindrical end piece with a circumferential knurling.

55. A medical fastening device in accordance with claim 40, wherein the sensor mount is arranged in the counterpiece.

56. A medical fastening device in accordance with claim 40, wherein the sensor mount has a cross-shaped or V-shaped configuration.

57. A medical fastening device in accordance with claim 40, wherein the sensor mount is provided with a cover.

58. A medical fastening device in accordance with claim 40 wherein the electromagnetic sensor is configured as at least two helically wound coils arranged at a finite angle in relation to one another.

59. A medical fastening device in accordance with claim 40, wherein the medical instrument is provided with a circumferential groove and a width of the carriage corresponds to an axial length of the circumferential groove of the medical instrument.

60. A medical fastening device in accordance with claim 59, wherein the medical instrument lies in an area of the circumferential groove flatly on the second end section of the depression of the holding part and/or on the groove of the carriage.

* * * * *